United States Patent
Bian et al.

(10) Patent No.: US 9,260,466 B2
(45) Date of Patent: Feb. 16, 2016

(54) USE OF A FLAVANOL GLYCOSIDE FOR SUPPRESSING ACTIVATION OF STELLATE CELLS

(71) Applicant: Hong Kong Baptist University, Kowloon (HK)

(72) Inventors: Zhaoxiang Bian, Kowloon Tong (HK); Siu Wai Tsang, Kowloon Tong (HK); Hongjie Zhang, Kowloon Tong (HK); Yegao Chen, Kowloon Tong (HK); Aiping Lu, Kowloon Tong (HK); Albert Sun-Chi Chan, Kowloon Tong (HK); Hongxi Xu, Kowloon Tong (HK); Shilin Chen, Kowloon Tong (HK); Dajian Yang, Kowloon Tong (HK)

(73) Assignee: Hong Kong Baptist University (HK)

( * ) Notice: Subject to any disclaimer, the term of this patent is extended or adjusted under 35 U.S.C. 154(b) by 61 days.

(21) Appl. No.: 13/899,713

(22) Filed: May 22, 2013

(65) Prior Publication Data

US 2014/0348965 A1   Nov. 27, 2014

(51) Int. Cl.
| | |
|---|---|
| *A61K 36/11* | (2006.01) |
| *C07H 17/065* | (2006.01) |
| *A61K 31/7048* | (2006.01) |
| *A61K 36/12* | (2006.01) |

(52) U.S. Cl.
CPC .......... *C07H 17/065* (2013.01); *A61K 31/7048* (2013.01); *A61K 36/12* (2013.01); *A61K 2236/00* (2013.01)

(58) Field of Classification Search
CPC ................................ C07C 67/08; C07C 69/16
USPC ......................................................... 424/725
See application file for complete search history.

(56) References Cited

U.S. PATENT DOCUMENTS 7,550,160 B2 *  6/2009  Wu et al. ........................ 424/725

FOREIGN PATENT DOCUMENTS

CN           102058627 A  *  5/2011

OTHER PUBLICATIONS

Wei et al. (Chalcone derivatives from the fern Cyclosorus parasiticus and their anti-proliferative activity, Food and Chemical Toxicology 60 (2013) 147-152).*
Zhao et al. (Antioxidant Flavonoid Glycosides from Aerial Parts of the Fern Abacopteris penangiana, J. Nat. Prod. 2007, 70, 1683-1686).*
Van Laethem, J., Robberecht, P., ReSibois, A and Deviere, J. Transforming Growth Factor β Promotes Development of Fibrosis After Repeated Courses of Acute Pancreatitis in Mice. Gastroenterology 1996;110:576-582.
Yoo MD, B. M., Yeo PhD, M., Oh PhD, T. Y., Choi MD, J. H., Kim MD, W. W., Kim MD, J. H., Cho MD, S. W., Kim PhD, J. K., and Hahm PhD, K. Amelioration of Pancreatic Fibrosis in Mice With Defective TGF-b Signaling. Pancrease vol. 30, No. 30, Apr. 2005.
Zhao, Z., Ruan, J. Jin, J., Zou, J., Zhou, D., Fang, W. and Zeng, F. Flavan-4-ol Glycosides from the Rhizomes of Abacopteris penangiana. © 2006 American Chemical Society and American Society of Pharmacognosy.
Apte, M. V., Haber, P.S., Applegate, I. D., Norton, McCaughan, G. W., Korsten, M. A., Pirola, R. C., and Wilson, J. S. Mechanisms of Pancreatic Fibrosis. Gut 1998;43:128-133.
Apte, M. V. and Wilson, J. S. Mechanisms of Pancreatic Fibrosis. Review Article Dig Dis 2004;22:273-279.
Chen, J., Chen, X., Lei, Y., Wei, H., Xiong, C., Liu, Y., Fu, W., and Ruan, J. Vascular protective potential of the total flavanol glycosides from Abacopteris penangiana via modulating nuclear transcription factor-KB signaling pathway and oxidative stress. Journal of Ethnopharmacology 136 (2011) 217-223.
Erkan, M., Adler, G., Apte, M. V., Bachem, M. G., Buchholz, M., Detlefsen, S., Esposito, L, Friess, H., Gress, T. M., Habisch, H., Hwang, R. F., Jaster, R., Kleef, J., Kloppel, G., Kordes, C., Logsdon, C. D., Masamune, A., Michalski, C. W., Oh, J., Phillips, P. A., Pinzani, M., Reiser-Erkan, C., Tsukamoto, H., and Wilson, J. StellaTUM: current consensus and discussion on pancreatic stellate cell research. Leading Article: Erkan M, Adler G, Apte MV, et al. Gut (2011).
Hu, Q., Noor, M., Wong, Y. F., Hylands, P. J., Simmonds, M. S. J., Xu, Q., Jiang, D., Hendry, B. M., and Xu, Q. In vitro anti-fibrotic activities of herbal compounds and herbs. Nephrol Dial Transplant (2009) 24: 3033-3041.
Lee, Y. S., Kim, J. K., Bae, Y. S., Won, M., Kang, I., and Lim, S. S. Inhibitory effect of glucodistylin from the bark of *Quercus acutissima* on human recombinant aldose reductase and sorbitol accumulation. Arch Pharm Res vol. 34, No. 2, 211-215, 2011.
Patel, M. and Fine, D. R. Fibrogenesis in the Pancreas After Acinar Cell Injury. Scandinavian Journal of Surgery 94: 108-111, 2005.
Schneider, E., Schmid-Kotsas, A., Zhao, J., Weidenbach, H., Schmid, R. M., Menke, A., Adler, G., Waltenberger, J., Grunert, A., and Bachem, M. G. Identification of mediators stimulating proliferation and matrix synthesis of rat pancreatic stellate cells. Am J Physiol Cell Physiol 281:C532-0543, 2001.
Sparmann, G., Hohenadl, C., Tornoe, J., Jaster, R., Fitzner, B., Koczan, D., Thiesen, H., Glass, A., Winder, D., Liebe, S., and Emmrich, J. Generation and characterization of immortalized rat pancreatic stellate cells. Am J Physiol Gastrointest Liver Physiol 287:G211-G219, 2004.
Tang, D., Wang, D., Yuan, Z., Xue, X., Zhang, Y., An, Y., Chen, J., Tu, M., Lu, Z., Wei, J., Jiang, K., and Miao, Y. Persistent activation of pancreatic stellate cells creates a microenvironment favorable for the malignant behavior of pancreatic ductal adenocarcinoma. Int. J. Cancer: 132, 993-1003 (2013) VC 2012 UICC.

* cited by examiner

*Primary Examiner* — Chris R Tate
*Assistant Examiner* — Randall Winston
(74) *Attorney, Agent, or Firm* — Renner Kenner Greive Bobak Taylor & Weber

(57) ABSTRACT

A method for suppressing activation of pancreatic stellate cells of a subject includes administering a composition comprising a therapeutically effective amount of Eruberin A. A method of preventing, alleviating or treating pancreatic tumors or pancreatic tumors related diseases includes administering a composition comprising a therapeutically effective amount of Eruberin A. The Eruberin A may be extracted from *Pronephrium penangianum*.

6 Claims, 3 Drawing Sheets

USE OF A FLAVANOL GLYCOSIDE FOR SUPPRESSING ACTIVATION OF STELLATE CELLS

FIELD OF INVENTION

This invention relates to the usage of a natural compound for suppressing the activation of stellate cells. Particularly, this invention relates to the usage of a naturally derived flavanol glycoside for suppressing activation of pancreatic stellate cells (PSCs).

BACKGROUND OF INVENTION

According to a number of recent studies, such as Patel M, Fine D R. *Fibrogenesis in the pancreas after acinar cell injury. Scand J. Surg.* 2005; 94(2):108-111 and Erkan M, Adler G, Apte M V, Bachem M G, Buchholz M, Detlefsen S, Esposito I, Friess H, Gress T M, Habisch H J, Hwang R F, Jaster R, Kleeff J, Kloppel G, Kordes C, Logsdon C D, Masamune A, Michalski C W, Oh J, Phillips P A, Pinzani M, Reiser-Erkan C, Tsukamoto H, Wilson J. Stella *TUM: current consensus and discussion on pancreatic stellate cell research. Gut.* 2012 February; 61(2): 172-178, it is known that pancreatic stellate cells (PSCs) play a critical role in the development of pancreatic fibrosis which is often accompanied with chronic pancreatitis (CP) and desmoplastic reaction of pancreatic cancer. Typically, PSCs localized at the periacinar region of the exocrine pancreas are quiescent under normal condition. As reported in Apte M V, Haber P S, Applegate T L, Norton I D, McCaughan G W, Korsten M A, Pirola R C, Wilson J S. *Periacinar stellate shaped cells in rat pancreas: identification, isolation, and culture. Gut.* 1998 July; 43(1): 128-33, upon injury or inflammation, these PSCs tend to lose their fat-droplets and transform into myofibroblast-like phenotype which can be identified with the presence of α-smooth muscle actin (α-SMA or Acta2). Also reported in Apte M V, Wilson J S. *Mechanisms of pancreatic fibrosis. Dig Dis.* 2004; 22(3):273-9. and Yoo B M, Yeo M, Oh T Y, Choi J H, Kim W W, Kim J H, Cho S W, Kim S J, Hahm K B. *Amelioration of pancreatic fibrosis in mice with defective TGF-beta signaling. Pancreas.* 2005 April; 30(3):e71-9, the formation of these fibrotic stress filaments actually elicits the cascade of tissue repairing mechanisms in response to pro-fibrotic and/or pro-inflammatory mediators such as transforming growth factor-beta (TGF-β), tumor necrosis factor-alpha (TNF-α) and interleukin 1 beta (IL-1β) being generated upon tissue injury. As identified by van Laethem J L, Robberecht P, Resibois A, Deviere J. *Transforming growth factor beta promotes development of fibrosis after repeated courses of acute pancreatitis in mice. Gastroenterology.* 1996 February; 110(2):576-82, once the PSCs are activated, they produce massive extracellular matrix (ECM) proteins, namely fibronectin 1 (Fn1) and type I collagen (Col I-α1), for the purpose of tissue repairing as well as regeneration. In fact, properties of stellate cells in the pancreas are similar to those present in other organs such as liver, kidney and lung. Not merely limiting to the pancreas, the production and deposition of ECM in an imbalanced fashion in an organ causes scarring of the parenchyma that is replaced by connective tissues. This indeed leads to permanent morphological damages of the organ. Progressive fibrosis possibly results in anatomical anomalies, organ failure or cancer. Therefore, the abolishment of the overwhelmed tissue repairing mechanism is crucial to the treatment of fibrosis and the associated impairments of the organ. In the case of pancreatic fibrosis, the activation of PSCs plays a central tread in the synthesis, deposition, formulation and remodeling of the various ECM proteins and fibrogenic mediators. It is also known, as reported in Tang D, Wang D, Yuan Z, Xue X, Zhang Y, An Y, Chen J, Tu M, Lu Z, Wei J, Jiang K, Miao Y. *Persistent activation of pancreatic stellate cells creates a microenvironment favorable for the malignant behavior of pancreatic ductal adenocarcinoma. Int J Cancer.* 2013 Mar. 1; 132(5):993-1003 that by maintaining high levels of ECM proteins and other pro-inflammatory and/or pro-fibrotic factors, PSCs create desmoplasia and a hypoxic microenvironment that promotes the initiation, development, evasion of immune surveillance, invasion, metastasis and resistance to chemoradiation of pancreatic ductal adenocarcinoma (PDAC). PDAC is one of the most common malignant tumors with poor prognosis due to extremely high malignancy, low rate of eligibility for surgical resection and chemoradiation resistance. Increasing evidence indicates that the interaction between activated PSCs and PDAC cells plays an important role in the development of PDAC. Therefore, targeting the interaction between PSCs and PDAC cells, and/or by suppressing the activation of PSCs, may represent novel therapeutic approaches to advanced PDAC, especially therapies that target PSCs of the pancreatic tumor microenvironment.

TGF-β has been reported by previous in-vitro and in-vivo studies such as Hu Q, Noor M, Wong Y E, Hylands P J, Simmonds M S, Xu Q, Jiang D, Hendry B M, Xu Q. *In vitro anti-fibrotic activities of herbal compounds and herbs. Nephrol Dial Transplant.* 2009 October; 24(10):3033-41 and Schneider E, Schmid-Kotsas A, Zhao J, Weidenbach H, Schmid R M, Menke A, Adler G, Waltenberger J, Grünert A, Bachem M G. *Identification of mediators stimulating proliferation and matrix synthesis of rat pancreatic stellate cells. Am J Physiol Cell Physiol.* 2001 August; 281(2):C532-43, that it is as being one of the potent inducers to the activation of PSCs. In cultured LTC-14 cells, which is an immortalized rat PSC line established by Sparmann G et al as described in Sparmann, G, Hohenadl, C., Tornoe, J., Jaster, R., Fitzner, B., Koczan, D., Thiesen, H. J., Glass, A., Winder D., Liebe, S., and Emmrich, J. *Generation and characterization of immortalized rat pancreatic stellate cells. Am J Physiol Gastrointest Liver Physiol.* 2004:287, G211-219, the mRNA and protein levels of the fibrotic filament α-SMA and the production of ECM proteins namely Fn1 and Col I-α1 were remarkably elevated in response to the exogenous addition of recombinant TGF-β (5 ng/mL) in the culturing microenvironment.

SUMMARY OF INVENTION

In accordance with a first aspect of the present invention, there is provide a method for suppressing activation of stellate cells present in an internal organ of a subject by administering to the subject a composition comprising a therapeutically effective amount of:
 an extract from a fern belonging to the Thelypteridaceae family;
 a flavanol glycoside which comprises a compound of formula (1):

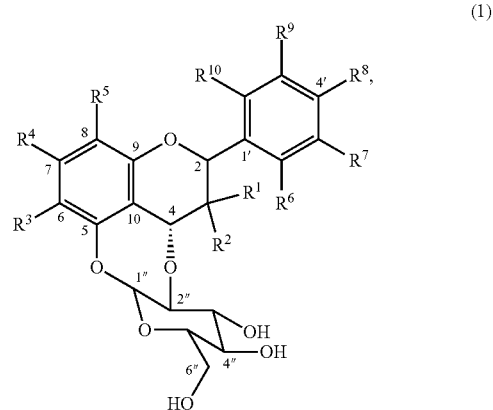

(1)

wherein $R^1$, $R^2$, $R^4$, $R^6$, $R^7$, $R^8$, $R^9$, and $R^{10}$ are each independently hydrogen, hydroxy or $C_{1-6}$ alkoxy whereas $R^3$ and $R^5$ are each independently $C_{1-6}$ alkyl; and derivatives or chemical variants thereof;

or a mixture of said extract, compound, derivatives and/or chemical variants thereof.

In an embodiment of the first aspect, the flavanol glycoside comprises a 2,3-dehydroflavonoid of formula (2):

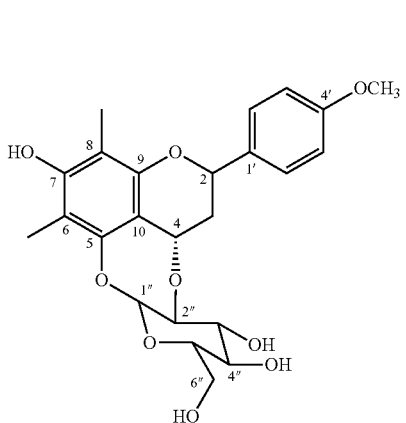

(2)

and derivatives or chemical variants thereof;

or a mixture of said flavanol glycoside, its derivatives and/or chemical variants thereof.

In an embodiment of the first aspect, the 2,3-dehydroflavonoid is Eruberin A.

In an embodiment of the first aspect, the subject is a human.

In an embodiment of the first aspect, the fern is *Pronephrium penangianum* and related sub-species.

In an embodiment of the first aspect, the internal organ comprises pancreas, liver, kidney or lung.

In accordance with a second aspect of the present invention, there is provided a method for preventing, alleviating or treating pancreatic tumors or pancreatic tumors related diseases by administering to a subject in needs thereof a composition comprising a therapeutically effective amount of:

an extract from a fern belonging to the Thelypteridaceae family;

a flavanol glycoside which comprises a compound of formula (1):

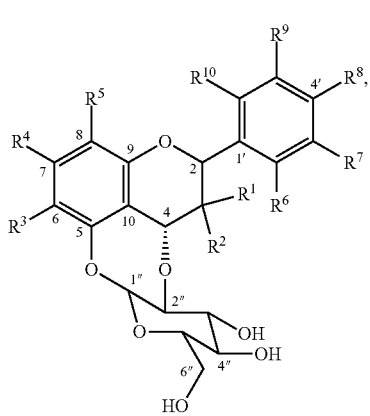

(1)

wherein $R^1$, $R^2$, $R^4$, $R^6$, $R^2$, $R^8$, $R^9$, and $R^{10}$ are each independently hydrogen, hydroxy or $C_{1-6}$ alkoxy whereas $R^3$ and $R^5$ are each independently $C_{1-6}$ alkyl; and derivatives or chemical variants thereof;

or a mixture of said extract, compound, derivatives and/or chemical variants thereof.

In an embodiment of the second aspect, the flavanol glycoside comprises a 2,3-dehydroflavonoid of formula (2):

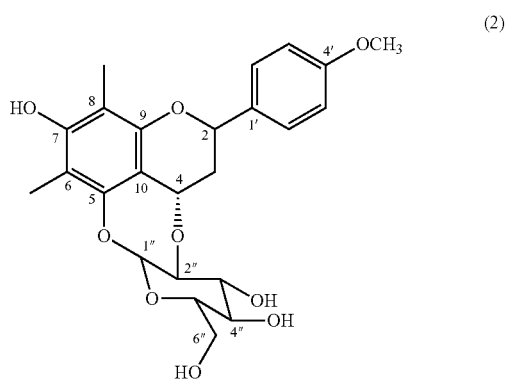

(2)

and derivatives or chemical variants thereof;

or a mixture of said flavanol glycoside, its derivatives and/or chemical variants thereof.

In an embodiment of the second aspect, the 2,3-dehydroflavonoid is Eruberin A.

In an embodiment of the second aspect, the subject is a human.

In an embodiment of the second aspect, the fern is *Pronephrium penangianum* and related sub-species.

In an embodiment of the second aspect, the pancreatic tumors or pancreatic tumors related diseases comprise pancreatic ductal adenocarcinoma.

In accordance with a third aspect of the present invention, there is provided a method of extracting and isolating a flavanol glycoside from *Pronephrium penangianum* comprising:

extracting a *Pronephrium penangianum* sample with a first solvent to form one or more first extracts;

treating the one or more first extracts to form a crude extract;

extracting the crude extract with a second solvent to form a second extract;

separating the second extract by using a first column chromatography to form at least one fraction;

separating the at least one fraction by using a second column chromatography to form at least one subfraction;

purifying the at least one subfraction to yield the flavanol glycoside.

In an embodiment of the third aspect, the flavanol glycoside comprises a 2,3-dehydroflavonoid.

In an embodiment of the third aspect, the 2,3-dehydroflavonoid is a Eruberin A.

In an embodiment of the third aspect, the *Pronephrium penangianum* sample is a dried whole plant of *Pronephrium penangianum*, or a dried part of *Pronephrium penangianum*.

In an embodiment of the third aspect, the first solvent is ethanol.

In an embodiment of the third aspect, the second solvent is ethyl acetate.

In an embodiment of the third aspect, the treating step comprises filtering, combining, concentrating or a mixture thereof.

BRIEF DESCRIPTION OF DRAWINGS

The above and other objects and features of the present invention will become apparent from the following description of the invention, when taken in conjunction with the accompanying drawings, in which.

DETAILED DESCRIPTION OF INVENTION

Figure 1:
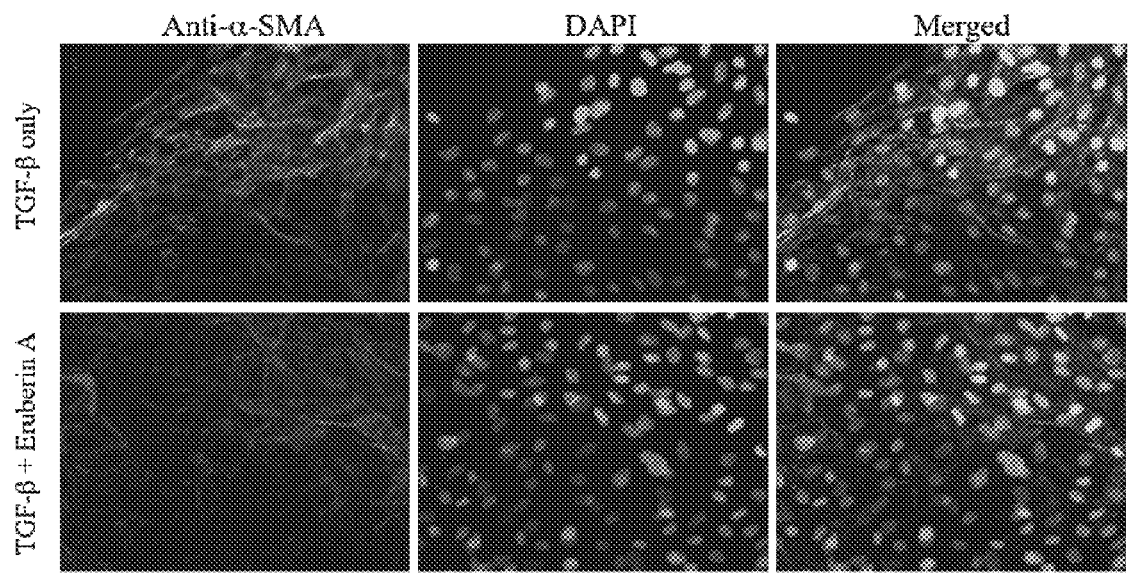
FIG. 1 shows the immunofluorescent images of LTC-14 cells showing the suppressive effects of Eruberin A on the immunoreactivities of α-SMA.

A preferred embodiment of the present invention relates to a method for suppressing activation of stellate cells present in an internal organ of a subject by administering to the subject a composition comprising a therapeutically effective amount of:

an extract from a fern belonging to the Thelypteridaceae family;

a flavanol glycoside of the following formula (Compound 1):

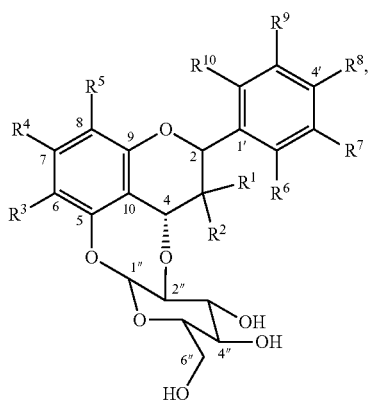

Compound 1 wherein $R^1$, $R^2$, $R^4$, $R^6$, $R^7$, $R^8$, $R^9$, and $R^{10}$ are each independently hydrogen, hydroxy or $C_{1-6}$ alkoxy whereas $R^3$ and $R^5$ are each independently $C_{1-6}$ alkyl; and derivatives or chemical variants thereof;

or a mixture of said extract, compound, derivatives and/or chemical variants thereof.

The term "$C_{1-6}$ alkyl", alone or in combination with other groups, means a branched or straight-chain monovalent alkyl moiety, having 1, 2, 3, 4, 5 or 6 carbon atoms. Preferably, the term alkyl includes methyl, ethyl, n-propyl, isopropyl, n-butyl, s-butyl and t-butyl. In particular, the alkyl moiety is preferred to have 1, 2, 3 or 4 carbon atoms.

The term "$C_{1-6}$ alkoxy", alone or in combination with other groups, means the group —O-alkyl, wherein alkyl is a $C_{1-6}$ alkyl.

The internal organ can be, for example, pancreas, liver, kidney and lung of a subject. The subject can be a human subject.

Preferably, the flavanol glycoside is a 2,3-dehydroflavan-4-ol glycosides such as Eruberin A (see Compound 2), which is a 2,3-dehydroflavonoid that suppresses the activation of pancreatic stellate cells (PSCs).

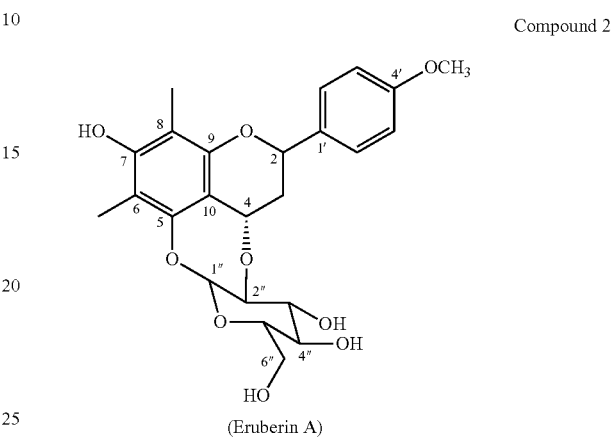

Compound 2

(Eruberin A)

In the present invention, Eruberin A was isolated from the dried whole plant of *Pronephrium penangianum* (*P. penangianum*), which is a fern belongs to the Thelypteridaceae family. Alternatively, Eruberin A can also be isolated from a dried specimen of *Pronephrium penangianum*. Under the genus *Pronephrium*, among the 91 species found in the world, 18 of them are widely distributed in Henan, Hubei, Jiangxi, Guizhou, and Yunnan provinces of China, majorly in damp places. *P. penangianum* has been used as a traditional medicine since ancient times in China. The rhizomes of this fern are used for the treatment of metrorrhagia whereas the leaves are used for the management of hypomenorrhea and amenorrhea. Previous phytochemical investigation such as Zhao, Z. X; Ruan, J. L.; Jin, J.; Zou, J.; Zhou, D. N; Fang, W; Zeng, F B. *Flavan-4-ol Glycosides from the Rhizomes of Abacopteris penangiana*. J. Nat. Prod. 2006, 69, 265 demonstrated that flavanol glycosides extracted from *P. penangianum* possess antioxidant activities, especially in diabetes-associated oxidative stress conditions as reported in Chen J, Chen X, Lei Y, Wei H, Xiong C, Liu Y, Fu W, Ruan J. *Vascular protective potential of the total flavanol glycosides from Abacopteris penangiana via modulating nuclear transcription factor-κB signaling pathway and oxidative stress*. J. Ethnopharmacol. 2011 Jun. 14; 136(1):217-23 and Lee Y S, Kim J K, Bae Y S, Won M H, Kang I J, Lim S S. *Inhibitory effect of glucodistylin from the bark of Quercus acutissima on human recombinant aldose reductase and sorbitol accumulation*. Arch Pharm Res. 2011 February; 34(2):211-5.

Experimental and Characterization

Extraction and Isolation.

The dried whole plant of *P. penangianum* (0.5 kg) was extracted with 95% ethanol (EtOH) at room temperature for 5 times. Each extraction was performed with 3.0 L of the 95% ethanol under a duration of 2 days. The EtOH extracts were filtered, combined and concentrated under reduced pressure to give a crude extract (103 g), which was in the form of a suspension in water (1.0 L). The crude extract was extracted further with ethyl acetate (AcOEt) for 6 times, each with 1.0 L of ethyl acetate. The AcOEt-soluble fraction (13 g) was subjected to column chromatographic separation using silica gel (200-300 mesh) and eluting with a solvent mixture of petroleum ether/AcOEt 1:0 to 0:1 and methanol (MeOH) to give seven fractions (F1, F2, F3, F4, F4, F6 and F7). F4 (251 mg) was further separated by a MCI column chromatography eluting with a solvent mixture of MeOH/$H_2O$ 7:3 to 9:1 to give three subsequent subfractions (F4.1, F4.2 and F4.3). F4.2 (45 mg) was then purified with a Sephadex LH-20 column eluting with MeOH to yield purified Eruberin A (10.0 mg).

Structural Identification.

The purified Eruberin A was obtained as white needles. The molecular formula was established as $C_{24}H_{28}O_9$ as characterized by the Time-of-Flight Mass Spectrometry (TOF MS) (m/z 483 [M+Na]+) and $^1$H-NMR and $^{13}$C-NMR. The $^1$H-NMR spectrum showed two singlet methyl characteristic signals at $\delta$ 2.60, and 2.07, a methoxy singlet signal at $\delta$ 3.83, an anomeric proton signal at $\delta$ 5.15 (d, J=8.3 Hz), and four aromatic proton doublet signals at $\delta$ 7.43 (2H, d, J=8.5 Hz) and 6.96 (2H, d, J=8.5 Hz), suggesting a 1,4-disubstituted ring B. The $^{13}$C-NMR and Heteronuclear Single Quantum Coherence (HSQC) spectra revealed that the compound has one 1,4-disubstituted phenyl group and one fully substituted phenyl group and two aromatic methyl groups in the aglycon. A substructure, —CH—$CH_2$—CH—, was also established through the analysis of the $^1$H-$^1$H Correlation Spectroscopy (COSY) spectral data. In comparison with the literature data, the natural compound used in our study was identified as the known flavan-4-ol glycoside Eruberin A: $^1$H-NMR ($CD_3OD$, 500 MHz) $\delta$ 7.43 (2H, d, J=8.5 Hz, H-2', 6'), 6.96 (2H, d, J=8.5 Hz, H-3', 5'), 5.15 (1H, d, J=8.3 Hz, H-1"), 5.10 (1H, m, H-4), 4.97 (1H, d, J=4.3 Hz, H-2), 4.64 (1H, s, OH), 3.91, 3.68 (2H, m, H-6"), 3.83 (3H, s, $OCH_3$), 3.62 (1H, m, H-3"), 3.38 (1H, m, H-5"), 3.36 (1H, m, H-2"), 3.19 (1H, m, H-4"), 2.60 (3H, s, 6-$CH_3$), 2.32, 2.00 (2H, m, H-3), 2.07 (3H, s, 8-$CH_3$); $^{13}$C-NMR ($CD_3OD$, 125 MHz) $\delta$ 161.2 (s, C-4'), 156.4 (s, C-7), 153.2 (s, C-9), 151.7 (s, C-5), 135.2 (s, C-1'), 129.1 (d, C-2', 6'), 115.2 (d, C-3', 5'), 111.5 (s, C-6), 109.8 (s, C-8), 105.7 (s, C-10), 103.0 (d, C-1"), 79.3 (d, C-5"), 77.1 (d, C-3"), 76.3 (d, C-2"), 75.1 (d, C-2), 72.2 (d, C-4"), 67.5 (d, C-4), 63.4 (t, C-6"), 56.2 (q, 4'-$OCH_3$), 38.7 (t, C-3), 9.9 (q, 6-$CH_3$), 9.0 (q, 8-$CH_3$).

Evaluation of Biological Activities.

LTC-14 cells were cultured at 37° C. under a humidified condition of 95% air and 5% $CO_2$ in Iscove's Modified Dulbecco's Medium (IMDM) supplemented with 10% fetal bovine serum (FBS). Cells used in all the experiment were among passages 9 to 25. LTC-14 cells were seeded at a density of $1 \times 10^5$/well in a 12-well plate, and incubated with recombinant TGF-$\beta$ at 5 ng/mL and Eruberin A at 0, 0.5, 1, 5, 10 and 20 μg/mL in serum-free IMDM for 24 hours. Cells were then harvested for mRNA and protein extraction or subjected to Sirius Red/Fast Green staining or immunofluorescent staining.

mRNA samples from LTC-14 cells were extracted using Trizol reagent and subjected to a reverse transcription for cDNA synthesis. The synthesized cDNA was applied to amplifications with rat-specific primers for Tgf-$\beta$, Acta2, Col I-$\alpha$1 and Fn1 in the ABI ViiA 7 real-time PCR system (Applied Biosystems) using 2×SYBR Green PCR Master Mix (Applied Biosystems). The Ct value of gene of interest was normalized to the endogenous reference Gapdh and presented as $2^{-\Delta\Delta Ct}$ using the comparative Ct method.

Cytoplasmic and nuclear protein fractions of the LTC-14 cells were extracted using specific lysis buffers containing protease inhibitors. Cell lysates were loaded and separated by SDS-polyacrylamide gel electrophoresis. After wet electroblotting, proteins were transferred onto PVDF membranes (Bio-Rad), blocked with 5% non-fat milk, probed with antibodies and visualized by utilization of an ECL kit (GE Healthcare).

Amounts of collagen and non-collagenous proteins in LTC-14 cells were measured using the Sirius Red/Fast Green collagen staining kit (Chondrex Inc.) according to the manufacturer's instruction.

For immunofluorescent staining of α-SMA, LTC-14 cells were seeded at a density of $1 \times 10^5$ onto the poly-L-lysine-coated cover slips in a 24-well plate, incubated with TGF-$\beta$ at 5 ng/mL and Eruberin A at 0, 0.5, 1, 5, 10 and 20 μg/mL in serum-free IMDM for 24 hours. Cells were then fixed, blocked with 3% bovine serum albumin (BSA), probed with antibodies and mounted with fluorescence mounting medium containing 4',6-diamidino-2-phenylindole (DAPI). Images were captured using the Nikon microscope and analyzed by the SPOT advanced software.

Results and Discussion

As shown in FIG. 1, it is observed that the administration of Eruberin A, significantly attenuated the TGF-$\beta$-stimulated α-SMA expression. The immunofluorescent images of FIG. 1 revealed that the administration of TGF-$\beta$ (at 5 ng/mL) remarkably induced the formation of fibrotic stress filaments α-SMA in LTC-14 cells. Treatment with compound of Eruberin A at 10 μg/mL is shown to sufficiently suppress the immunoreactivities of α-SMA.

Figure 2:
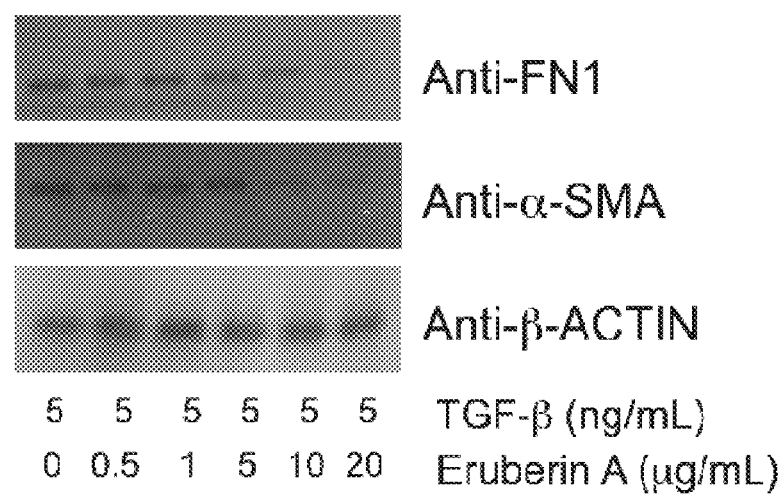
FIG. 2 shows the images of the Western blotting analysis showing the suppressive effects of Eruberin A on TGF-β-induced elevations of α-SMA and FN1 proteins in LTC-14 cells. Probing with the anti-β-ACTIN antibody was served as a loading reference of the cytoplasmic protein extract.

FIG. 2 further shows the suppressive effects of Eruberin A on TGF-$\beta$-induced elevations of α-SMA and FN1 proteins. LTC-14 cells were incubated with TGF-$\beta$ at 5 ng/mL and Eruberin A at 0, 0.5, 1.0, 5.0, 10 or 20 μg/mL for 24 hours in serum-free medium. From the Western blotting images, increased levels of α-SMA and FN1 proteins were observed upon TGF-$\beta$ stimulation. The addition of Eruberin A effectively attenuated the TGF-$\beta$-provoked elevations of α-SMA and FN1 proteins in a dose-dependent manner. Probing with the anti-$\beta$-ACTIN antibody was served as a loading reference of the cytoplasmic protein extract. The results as shown in FIG. 2 were the representatives of 3 individual experiments.

Figure 3:
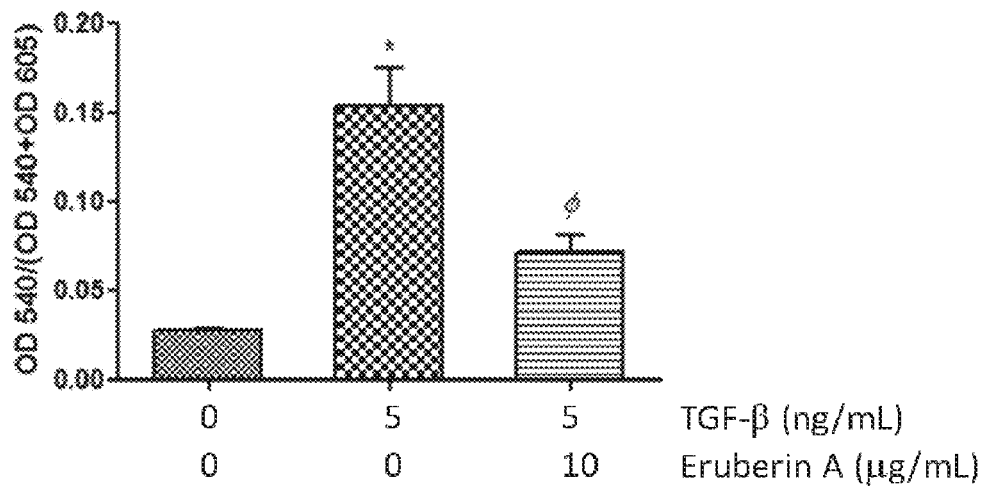
FIG. 3 shows the production of collagen, which is indicative of the progression of fibrogenesis, as a ratio of Sirius Red-stained collagenous proteins to Fast Green-stained non-collagenous proteins, on LTC-14 cells with and without the presence of Eruberin A.

FIG. 3 shows the production of collagen, which is indicative of the progression of fibrogenesis, as a ratio of Sirius Red-stained collagenous proteins to Fast Green-stained non-collagenous proteins. When LTC-14 cells were incubated with TGF-$\beta$ (5 ng/mL) alone, the production of collagen was significantly elevated; whereas when Eruberin A (10 μg/mL) was added, such elevation was notably suppressed.

In the graph of FIG. 3, * represented $p < 0.05$ when comparing with the control experiment with no treatment with TGF-$\beta$ or Eruberin A; whereas $\phi$ represented $p < 0.05$ when comparing to TGF-$\beta$ treatment (5 ng/mL) alone. The results were obtained by taking mean average of 3 individual batches of experiments.

Figure 4:
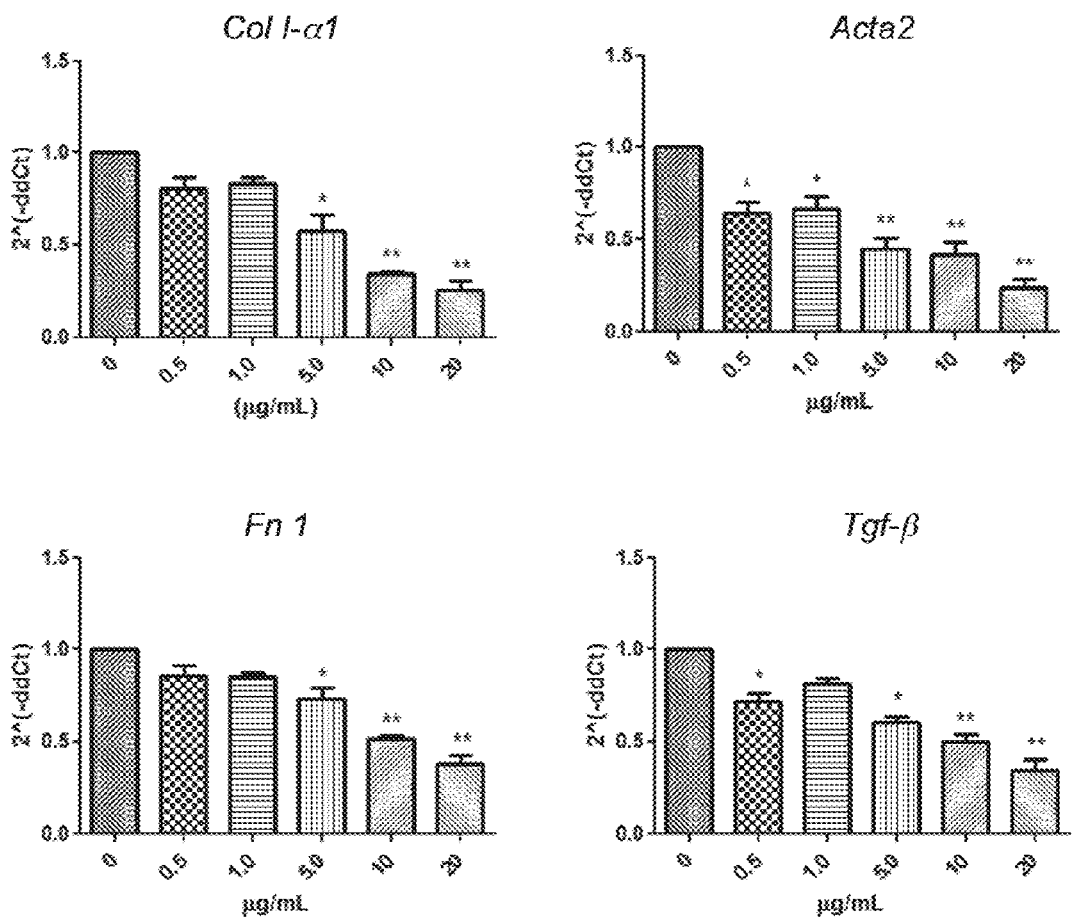
FIG. 4 shows the suppressive effects of Eruberin A on TGF-β-induced mRNA expression of fibrotic mediators of Col I-α1, Acta2, and Fn1 and Tgf- in LTC-14 cells.

FIG. 4 shows the suppressive effects of Eruberin A on TGF-$\beta$-induced mRNA expression of fibrotic mediators. LTC-14 cells were incubated with recombinant TGF-$\beta$ at 5 ng/mL and Eruberin A at 0, 0.5, 1.0, 5.0, 10 and 20 μg/mL for 24 hours in serum-free medium. The real-time quantitative PCR results demonstrated that Eruberin A significantly and dose-dependently suppressed the TGF-$\beta$-elevated mRNA expression levels of Col I-$\alpha$1, Acta2, and Fn1 and Tgf- in LTC-14 cells. Expression of the gene of interest was measured as a Ct value, normalized to the endogenous reference Gapdh and expressed as $2^{-\Delta\Delta Ct}$. As shown in the graphs of FIG. 4, * represented $p < 0.05$ and ** represented $p < 0.001$ when comparing with the control experiment which is treated with TGF-$\beta$ at 5 ng/mL only. The results were obtained by taking mean average from 3 individual batches of experiments. By means of MTT cell proliferation assay, no notable cytotoxicity was observed when Eruberin A was applied in the range of 0 to 20 μg/mL (results not shown). The $IC_{50}$ of this natural compound is approximately 10 μg/mL based on its suppressive effects on the mRNA expression of α-SMA.

Figure 5:
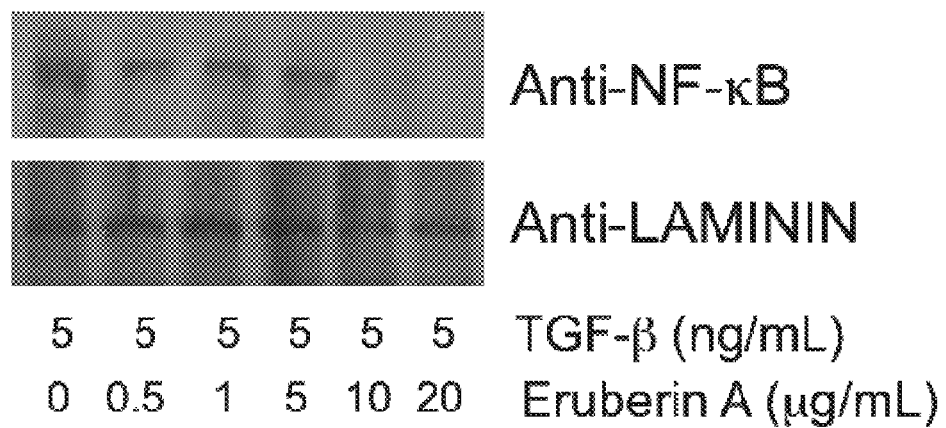
FIG. 5 shows the images of the Western blotting analysis showing suppressive effect of Eruberin A on NF-κB activation.

The down-regulation of associated fibrotic mediators by Eruberin A was probably due to the suppressed translocation of NF-κB, which is the dominant signaling pathway for modulating the robust cascades of fibrosis and inflammations. FIG. 5 shows the suppressive effect of Eruberin A on NF-κB activation. The Western blotting analysis demonstrated that the nuclear translocation of NF-κB was significantly decreased by the treatments of Eruberin A when comparing to the TGF-β-treated control. LAMININ was served as a loading reference for the nuclear protein extract. Images shown in FIG. 5 were the representatives of 3 individual experiments.

Accordingly, the present invention revealed that the administration of a flavonoid that contains 2,3-dehydroflavan-4-ol glycosides such as Eruberin A significantly attenuated the TGF-β-stimulated α-SMA expression, and the synthesis of fibronectin and collagenous proteins in the in-vitro model of rat PSCs. Not limited to the translation levels, the suppressive effects of Eruberin A on fibrotic mediators are as well subject to transcriptional levels as the mRNA expression levels of Col I-α1, Acta2, Fn1 and Tgf-β are all significantly decreased. By means of MTT cell proliferation assay, no notable cytotoxicity was observed when Eruberin A was applied in the range of 0 to 20 μg/mL. The $IC_{50}$ of this natural compound is approximately 10 μg/mL based on its suppressive effects on the mRNA expression of α-SMA. Most importantly, the down-regulation of associated fibrotic mediators by Eruberin A was probably due to the suppressed translocation of NF-κB, which is the dominant signaling pathway for modulating the robust cascades of fibrosis and inflammations. It is believed that the substantial decrease of PSC pro-fibrotic activities in-vitro is indicative to the attenuation of pancreatic fibrogenesis in-vivo.

It is envisaged that the present invention is applicable to the usage of Eruberin A in treatments of fibrosis and fibrotic conditions in a human subject. More particularly, it is envisaged that this invention is applicable to the usage of a natural flavanol glycoside compound that contains 2,3-dehydroflavan-4-ol glycosides such as Eruberin A, as an anti-fibrotic agent in suppressing the activation of pancreatic stellate cells (PSCs) in a human subject. It is further envisaged that this invention can be applied to the management of pancreatic fibrosis of a human subject, which is often accompanied with chronic pancreatitis (CP) and desmoplastic reaction of pancreatic cancer. It is also envisaged that this invention has applications in preventing or alleviating or treating pancreatic tumors or pancreatic tumors related diseases in a human subject, in which the pancreatic tumors or pancreatic tumors related diseases may comprise pancreatic ductal adenocarcinoma.

If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the reminder of the disclosure in any way whatsoever. Without further elaboration, it is believed that one skilled in the art can, based on the description herein, utilize the present invention to its fullest extend. All publications recited herein are hereby incorporated by reference in their entirety. However, citation or identification of any reference in this section or any other section of this application shall not be construed as an admission that such reference is available as prior art for the present application.

Those skilled in the art will appreciate that the invention described herein is susceptible to variations and modifications other than those specifically described.

The invention claimed is:

1. A method for suppressing a fibrotic mediator of stellate cells present in an internal organ of a subject in need thereof by administering to the subject a composition comprising a therapeutically effective amount of:
a flavanol glycoside which comprises a compound of formula (1):

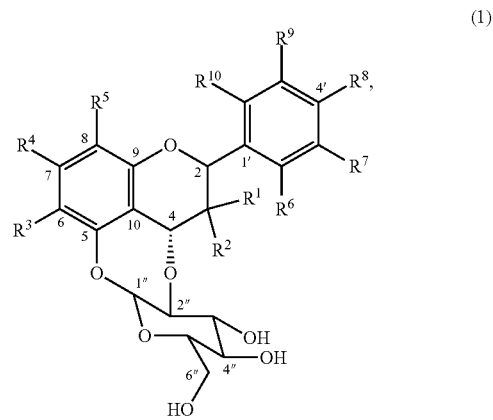

wherein $R^1$, $R^2$, $R^4$, $R^6$, $R^7$, $R^8$, $R^9$, and $R^{10}$ are each independently hydrogen, hydroxy or $C_{1-6}$ alkoxy whereas $R^3$ and $R^5$ are each independently $C_{1-6}$ alkyl.

2. The method according to claim 1 wherein the flavanol glycoside comprises a 2,3-dehydroflavonoid of formula (2):

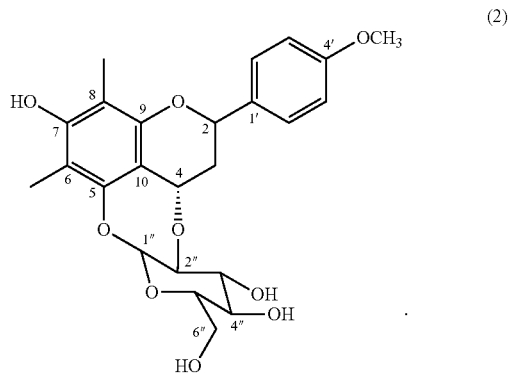

3. The method according to claim 2, wherein the 2,3-dehydroflavonoid is Eruberin A.

4. The method according to claim 1 wherein the subject is a human.

5. The method according to claim 1 wherein the composition further comprises a fern extract obtained from *Pronephrium penangianum* and related sub-species.

6. The method according to claim 1 wherein the internal organ comprises pancreas, liver, kidney or lung.

* * * * *